United States Patent [19]
Bradley et al.

[11] Patent Number: 6,080,899
[45] Date of Patent: Jun. 27, 2000

[54] METHOD OF PRODUCING FLUORINATED ORGANIC COMPOUNDS

[75] Inventors: David E. Bradley; Kevin Benson; David Nalewajek; Alagappan Thenappan, all of Erie County, N.Y.

[73] Assignee: AlliedSignal Inc., Morristown, N.J.

[21] Appl. No.: 09/236,880

[22] Filed: Jan. 25, 1999

[51] Int. Cl.[7] ........................................ C07C 17/08
[52] U.S. Cl. .......................................... 570/167; 570/168
[58] Field of Search ................................ 570/167, 168

[56] References Cited

U.S. PATENT DOCUMENTS 5,811,604  9/1998  Benson et al. ........................... 570/167

FOREIGN PATENT DOCUMENTS 2659046  7/1977  Germany ................................ 570/167

*Primary Examiner*—Alan Seigel
*Attorney, Agent, or Firm*—Jay P. Friedenson; Colleen D. Szuch; Marie L. Collazo

[57] ABSTRACT

A process for producing a fluorinated organic compound comprising: (a) reacting an organic starting material with hydrogen fluoride in the presence of a fluorination catalyst and an HFC reaction solvent to produce a product stream containing the fluorinated organic compound wherein the reaction solvent has a boiling point higher than that of the fluorinated organic compound; and (b) recovering the fluorinated organic compound from the product stream.

19 Claims, No Drawings

METHOD OF PRODUCING FLUORINATED ORGANIC COMPOUNDS

FIELD OF INVENTION

The invention relates generally to a process for preparing fluorinated organic compounds. More specifically, the present invention relates to a liquid-phase, catalytic hydrofluorination process for preparing hydrofluorocarbons (HFCs) and hydrochlorofluorocarbons (HCFCs) from their more-chlorinated precursors.

BACKGROUND OF THE INVENTION

The production of fluorinated organic compounds, such as HFCs and HCFCs, is well known in the art. Among the more widely-used fluorination methods is liquid-phase, catalytic fluorination which is of particular interest herein. In this type of fluorination, a chlorinated organic precursor is reacted with anhydrous hydrogen fluoride (HF) in a reactor in the presence of a catalyst and under conditions sufficient to form a fluorinated organic compound. The fluorinated product tends to be more volatile then the chlorinated precursor, and is separated from the reaction mixture by distillation, along with the principal byproduct, hydrogen chloride (HCl).

Although widely used, conventional liquid-phase fluorination suffers from several shortcomings, one of the more significant being the compromise between high reaction rates and extensive corrosion to the reactor vessel. More specifically, it is common for a high concentration of highly-corrosive catalyst to be used as a reaction solvent. With such a high concentration, specific reaction conditions must be maintained to avoid formation of unwanted byproducts and extensive corrosion of the reactor vessel, even those comprising corrosion-resistant alloys such as Inconel and Hastalloy. These specific reaction conditions, however, tend to be outside the range generally preferred for optimum reaction rates. Additionally, the concentration of HF must be minimized because the corrosivity of the reaction mixture increases dramatically with higher HF concentrations. Unfortunately, however, lower concentrations of HF also result in lower reaction rates and production suffers.

Aside from its corrosive effects, maintaining such a high concentration of catalyst also tends to be expensive, thus favoring the use of chlorinated catalysts, such as antimony pentachloride, which are less expensive, but also less effective than their fluorinated counterparts. Chlorinated catalysts also tend to undergo deactivation to a less reactive state under commonly-used reaction conditions. For example, at temperatures of about 90° to about 110° C., antimony (+V) halides will deactivate into a (+III) halide. The deactivation results in improper fluorination and a general reduction in product selectivity. To counteract the catalyst's deactivation, an oxidizing agent, such as chlorine, is added to regenerate the catalyst. The addition of chlorine, however, tends to contribute to corrosion. Additionally, excess chlorine in the reaction mixture promotes side reactions which produce by-products. Therefore, the addition of chlorine increases reactor corrosion and generates unwanted by-products.

Reactor corrosion can be reduced by using the fluorinated product as the reaction solvent. However, given the relatively-high volatilities of the fluorinated products, such as, HFC-41, 23, 32, and 143a, extremely high reaction pressures result under normal operating conditions. Such high pressures necessitate the use of high pressure-rated reactors (for example, rated for pressures greater than 500 psig) which can be prohibitively expensive.

Therefore, a need exists for a fluorination process that is less corrosive, generates fewer by-products and avoids the need for oxidizing agents and high reaction pressures. The present invention fulfils this need among others.

DETAILED DESCRIPTION OF THE PRESENT INVENTION

The present invention overcomes the problems of conventional liquid-phase fluorination by using an HFC reaction solvent having a boiling point higher than that of the fluorinated product. The HFC reaction solvent provides a homogeneous mixture of the reactants and catalyst to facilitate a high rate of reaction, while diluting the catalyst to levels that avoid significant corrosion to metal reactors. Furthermore, since the amount of catalyst required is reduced, the process promotes the use of more expensive, but more effective fully-fluorinated superacid catalysts. These fully-fluorinated superacid catalysts, such as pentafluorides of antimony, niobium and/or tantalum, tend not to be reduced to inactive states due to their high thermal stability relative to pentachlorides, thus, chlorine addition to the reaction system is not required. By avoiding the need for $Cl_2$ oxidizer, reactor corrosion and the generation of by-products is reduced relative to the use of antimony pentachloride. Using a reaction solvent having a boiling point higher than that of the fluorinated product also provides for a lower overall reaction pressure at a given temperature relative to reactions in which the fluorinated product is used as a reaction solvent.

In addition to reducing corrosion and pressure, diluting the reaction catalyst concentration reduces the reaction mixture's viscosity, thereby facilitating agitation, which leads to improved reaction rates and heat/mass transfer. The reaction solvent also tends to increase the heat capacity or "thermal inertia" of the reaction mixture, thereby acting as a heat sink and stabilizing reaction temperature.

The above-mentioned advantages and benefits of the present invention make it particularly well suited for continuous processes, although they apply to batch operations as well. Additionally, the present invention can be practiced using new or existing fluorination apparatus/processes arrangements.

One aspect of the invention is the provision of a process for producing a fluorinated organic compound using an HFC reaction solvent. In the preferred embodiment, the process comprises (a) reacting an organic starting material with hydrogen fluoride in the presence of a fluorination catalyst in an HFC reaction solvent to produce a product stream containing a fluorinated organic compound; and (b) recovering the fluorinated organic compound from the product stream.

Suitable HFC's used in the reaction solvent include those, which, individually or in combination with other compositions, impart one or more of the following properties to the reaction solvent.

First, the reaction solvent should be selected to provide for a largely-homogeneous reaction solution. As used herein, the term "reaction solution" refers to the solution formed by the reaction solvent and includes the HFC reaction solvent, catalyst, HF, intermediates and the organic starting material. The term "reaction mixture" refers to the mass contained in the reactor and includes the reaction solution as well as any liquid- or solid-phase substances not in solution. To effect a homogeneous reaction solution, anhydrous hydrogen fluoride should be miscible in the reaction solvent along with at least a portion of the organic starting material as well as at least a portion of the fluorination catalyst. A homogeneous reaction solution provides each molecule of starting material with an equal probability of encountering a "catalyst site" and thus reacting to form a more fluorinated molecule.

Second, the reaction solvent of the present invention should have a boiling point (b.p.) above that of the fluorinated product at the reaction conditions employed. Compounds having such relatively high boiling points tend to contribute less partial pressure to the overall reaction pressure under reaction conditions, especially as their portion of the reaction mixture increases. Preferably, the selected reaction solvent has a partial pressure and is used in such a concentration in the reaction mixture that the vapor pressure of the reactor system is below that which necessitates a high pressure-rated reactor vessel. More preferably, the reaction pressure is less than 300 psig, and even more preferably, the reaction pressure is less than 150 psig.

The boiling point of the reaction solvent should be significantly higher than that of the fluorinated organic product not only to minimize its partial pressure, but also to facilitate its separation from the fluorinated product. More specifically, there should be little, if any, formation of azeotropes or azeotrope-like compositions between the reaction solvent and the fluorinated organic product. This way, separation and purification are readily achievable through convenient, conventional techniques such as distillation, absorption and/or reaction (for example, reacting HCl by-product with a base). Accordingly, in the preferred embodiment, the reaction solvent has a boiling point that is no less than 40° C. above the boiling point of the fluorinated organic product under the reaction conditions employed, and more preferably no less than about 50° C. For example, in the preparation of difluoromethane (HFC-32 ), 1,1,1-trifluoroethane (HFC-143a ) and difluorochloromethane (HFC-22 ) at 150 psig, which have boiling points of −10, −5 and 0° C. respectively, reaction solvents having boiling points of at least 30° C. are preferred, and those of at least about 40° C. are more preferred.

Third, it is preferable that the reaction solvent have little or no reactivity with the starting materials, intermediates, or the fluorinated product. In other words, the reaction solvent should dilute the reaction constituents as mentioned above, but should not participate in the overall reaction except as a solvent. For example, the reaction solvent should be selected such that it does not contribute to chlorination of the organic starting material or to dehydrofluorination of the fluorinated product.

Fourth, it is preferable that the solvent be thermally and chemically stable under the conditions at which fluorination and product recovery occur. In particular, the preferred reaction solvent should not thermally degrade at the operating temperatures, which typically range from about 50° to about 250° C. Furthermore, the solvent should be chemically stable in the reaction mixture which typically comprises superacids and has a pH ranging from about 0 to about −15.

It has been found that hydrofluorocarbon alkanes tend to posses the above-mentioned properties/attributes. In a preferred embodiment, the reaction solvent comprises at least one HFC compound having the formula $C_xH_yF_z$, wherein $3 \geq x \geq 6$, $1 \leq y$, providing $(y+z)=2x+2$. More preferably, x is 3 and $1 \leq y \leq 4$, and, even more preferably, $2 \leq y \leq 3$. Still more preferably, the reaction solvent comprises at least one compound selected from the group consisting of 1,1,1,3,3,3-hexafluoropropane (HFC-236fa) and its isomers, 1,1,1,3,3-pentafluoropropane (HFC-245fa) and its isomers except for 1,1,1,2,2-pentafluoropropane (HFC-245cb). The most preferred is HFC-245fa.

In addition to their favorable solvency, stability and boiling points, these compounds are environmentally appealing. They are not chlorinated and thus do not contribute to the depletion of the ozone layer. Furthermore, they have reasonable atmospheric lifetimes, for example, less than 150 years for HFC-236fa and less than 15 years for HFC-245fa.

The concentration of the solvent(s) in the reaction mixture may vary, although too little leads to a more-corrosive reaction environment, while excessive dilution of the reaction mixture tends to reduce productivity. It has been found that the concentration of the reaction solvent in the reaction mixture is preferably from about 20 to about 80 weight percent, more preferably from about 30 to about 70 weight percent, and even more preferably from about 40 to about 60 weight percent.

Although any conventional fluorination catalyst can be used in the process of the present invention, the use of stronger superacid catalysts is facilitated by diluting the catalyst with the HFC reaction solvent. Preferred fluorination catalysts include, but are not limited to, halides and mixed halides of Group IVa, IVb, Va and Vb elements. More preferred fluorination catalysts include, for example, halides and mixed halides of Antimony (Sb), Arsenic (As), Niobium (Nb), Tantalum (Ta), Titanium (Ti), and Tin (Sn). Even more preferred catalysts include pentafluorides of Sb, Nb, and Ta. The most preferred fluorination catalyst is $SbF_5$.

The catalyst's overall concentration in the reaction mixture and its concentration relative to HF are important considerations in minimizing reactor corrosion. More specifically, under reaction conditions, the pentafluoride catalyst ($MF_5$) is converted into an active, soluble superacid catalyst according to the following reaction:

$$2\ HF + MF_5 \rightarrow [H_2F^+][MF_6^-] \qquad (1)$$

The superacid catalyst is very reactive and results in high reaction rates; however, it also is very corrosive. Nevertheless, it has been found that the superacid remains relatively non-corrosive in the presence of a large molar excess of HF and a relatively low concentration of catalyst in the reaction mixture. In a preferred embodiment, the concentration of catalyst in the reaction mixture is from about 0.5 to about 10 wt. %, more preferably from about 1 to about 5 wt. %, and even more preferably from about 2 to about 4 wt. %. Maintaining a relatively low molar ratio of catalyst to HF also is preferred because, if the catalyst to HF mole ratio becomes too high, the reaction solvent will become very corrosive to the reactor, even in a large amount of HFC solvent. The molar ratio of catalyst to HF in the reaction mixture is preferably from about 1:50 to about 1:200, and more preferably from about 1:75 to about 1:125.

The reaction solvent of the present invention is found to be highly effective in the production of a variety of fluorinated products. Preferably, the process of the present invention involves the production of a fluorinated compound having the formula $C_nH_mF_xCl_y$, wherein $1 \leq n \leq 7$, $x \geq 1$, and $(m+x+y) \leq (2n+2)$, and, more preferably, $1 \leq n \leq 3$. In an even more preferred embodiment, the fluorinated organic compound is HCFC-22, HFC-32 or 1,1,1-trifluoroethane (HFC-143a).

The organic starting material may be any compound that contains a carbon-bonded chlorine or other atom replaceable by fluorine and/or that contains a carbon-carbon unsaturated bond that is saturatable with fluorine. Suitable organic compounds include, for example, hydrochlorofluorocarbons (compounds containing carbon, chlorine, fluorine and hydrogen), hydrochlorocarbons (compounds containing carbon, chlorine and hydrogen), chlorofluorocarbons (compounds containing carbon, chlorine and fluorine), hydrofluorocarbons (compounds containing carbon, hydrogen and fluorine), and chlorocarbons (compounds containing carbon and chlorine) or mixtures of two or more thereof. Among the unsaturated compounds, preferred hydrochlorocarbons include, for example, 1,1-dichloroethene (HCC-1 130), preferred hydrochlorofluorocarbons include, for example, 1-chloro-1-fluoroethene (HCFC-1 131), and preferred hydrofluorocarbons include, for example, difluoroethene (HFC-1 132). Preferred saturated hydrochlorocarbons and hydrofluorochlororcarbons have the general formula $C_nH_mF_qCl_r$, wherein $1 \leq n \leq 7$, $q \geq 1$, and $(m+q+r) \leq (2n+2)$, more preferably, $1 \leq n \leq 3$, and, still more preferably, n=1 or 2. Highly preferred hydrochlorocarbons include, for example, dichloromethane (HCC-30), trichloromethane (HCC-20) and 1,1,1-trichloroethane (HCC-140a). Highly preferred hydrochlorofluorocarbons include, for example, chlorofluoromethane (HCFC-3 1), dichlorofluoromethane (HCFC-21), 1,1-dichloro-1-fluoroethane (HCFC-14 1b), and 1-chloro-1,1-difluoroethane (HCFC-142b). It is worthwhile noting that the hydrochlorofluorocarbons and the hydrofluorocarbon starting materials also may be produced as intermediates in the fluorination reaction.

The concentration of the organic starting material in the reaction mixture is preferably from about 0.1 to about 30 weight percent, and more preferably from about 5 to about 20 weight percent.

Substantially anhydrous hydrogen fluoride (HF) is the preferred fluorination agent. The presence of water in the reaction tends to deactivate the fluorination catalyst. As used herein, the term "substantially anhydrous" refers to a moisture content of less than about 0.05% by weight and preferably less than about 0.02% by weight. It should be understood, however, that the presence of water in the catalyst can be compensated for by increasing the amount of catalyst used.

Generally, a large molar excess of HF in the reaction mixture is preferred. The excess is needed to compensate for HF that is "lost" to the downstream processes, such as acid scrubbers. Although much of the initial loss is typically "recovered" as the solvent-HF azeotropes are refluxed back into the reactor or recycled from downstream distillation columns, the reactor nevertheless should be charged initially with a concentration of HF high enough to accommodate this initial loss. Once the reaction is underway, the feed rate of HF should be maintained to accommodate fluorination plus compensate for the unrecoverable component of HF lost to downstream processing. Accordingly, the mole ratio of HF to organic starting material in the reaction mixture is preferably at least about 5:1, and more preferably at least about 10:1.

Higher concentrations of HF are also preferred for maintaining a low molar ratio of a catalyst to HF to minimize the corrosive effects of superacid catalysts as described above. Accordingly, the preferred initial concentration of HF in the reaction mixture is about 30 to about 60 wt. % and, more preferably, from about 40 to about 50 wt. %.

Preferably, the process of the present invention is conducted continuously. When this invention is practiced in a continuous fashion, the organic starting material and hydrogen fluoride are continuously fed into a reaction mixture containing HF, solvent and catalyst. The reaction produces a product stream comprising the fluorinated product and hydrogen chloride, which are distilled out of the product stream, along with some portion of the solvent, HF, reaction intermediates and HF-solvent and HF-intermediate azeotropes. The HF, solvent, and intermediates are condensed and then recycled back into the reactor, while the HCl and product are purified further downstream.

The temperature under which a continuous process is conducted will depend upon the fluorinated product, the concentration of the product in the reaction solvent, the organic starting material as well as other operational choices/constraints known in the art. It has been found that suitable results are obtained at reaction temperatures ranging from about 25 to about 125° C. In general, "easier" fluorinations require lower reaction temperatures. An approximate order of ease in fluorination is given below for the preferred fluorinated products:

| EXAMPLE | |
|---|---|
| HFC-143a | (less difficult) |
| HCFC-22, HFC-23 | |
| HFC-32 | |
| HFC-41 | (more difficult) |

This example illustrates the fluorination of dichloromethane (HCC-30) with anhydrous HF, SbF5 as a fluorination catalyst and HFC-245fa as a solvent.

A 600 ml Hastalloy-C autoclave equipped with a magnetic stir drive and a thermocouple was initially charged with 5.8 g SbF5 (0.027 moles) and 55.8 g anhydrous HF (2.79 moles). The mixture was stirred at 25° C. for 30 minutes. The autoclave was then charged with 105.7 g of 1,1,1,3,3-pentafluoropropane (HFC-245fa, 0.79 moles) and stirred at the same temperature for an additional 20 minutes. Finally, after charging 44.5 g (0.52 moles) of dichloromethane, the autoclave was connected to a packed column/condenser assembly and the condenser was maintained at −5° C. The reaction mixture was heated with stirring to about 110° C. and maintained at that temperature for an additional 2.5h. During this period, the pressure in the autoclave was maintained between 400–450 psig by periodically venting the pressure in excess of 450 psig. Venting was performed from the condenser's top to an aqueous potassium hydroxide scrubber that was connected to a collection cylinder cooled with liquid nitrogen. After 4.5 h the autoclave was completely vented to the collection cylinder to give 133.1 g of product mixture. Gas chromatographic analysis of that mixture indicated the following (area percentages): HFC-32 (19.4%), HCFC-31 (2.3%), HFC-245fa (71.3%), HFC-1234 (1.0%) and HCC-30 (5.4%).

What is claimed is:

1. A process for producing a fluorinated organic compound comprising:

reacting an organic starting material with hydrogen fluoride in the presence of a fluorination catalyst and in a reaction solvent comprising at least one HFC compound having the formula $C_xH_yF_z$, wherein $3 \leq x \leq 6$, $z \geq 1$ and $y+z=2x+2$ to produce a product stream containing a fluorinated organic compound having the formula $C_nH_mF_qCl_r$, wherein $1 \leq n \leq 7$, $q \geq 1$ and $(m+q+r) \leq (2n+2)$, wherein said reaction solvent has a boiling point higher than that of said fluorinated organic compound; and recovering said fluorinated organic compound from said product stream.

2. The process of claim 1 wherein x is 3 and $1 \leq y \leq 4$.

3. The process of claim 1 wherein $2 \leq y \leq 3$.

4. The process of claim 1, wherein said HFC compound is selected from the group consisting of HFC-236 and its isomers, HFC-245ca, HFC-245fa and HFC-245ea.

5. The process of claim 4, wherein the HFC reaction solvent is HFC-245fa.

6. The process of claim 1, wherein said reaction solvent has a boiling point of no less than about 0° C.

7. The process of claim 6, wherein said reaction solvent has a boiling point of no less than about 10° C.

8. The process of claim 1, wherein the concentration of said reaction solvent is about 20 to about 80 wt. % of the reaction mixture.

9. The process of claim 1, wherein $1 \leq n \leq 3$.

10. The process of claim 9, wherein said fluorinated compound is selected from the group consisting of HCFC-22, HFC-32 and HFC-143a.

11. The process of claim 1, wherein said fluorinated compound is selected from the group consisting of HCFC-22, HFC-32 and HFC-143a, and wherein said reaction solvent is selected from the group consisting of HFC-236, its isomers, HFC-245ca, HFC-245fa and HFC-245ea.

12. The process of claim 11, wherein said fluorinated compound is HFC-32, the reaction solvent is HFC-245fa.

13. The process of claim 11, wherein the vapor pressure of the reaction mixture is no greater than about 300 psig.

14. The process of claim 1, wherein the vapor pressure of the reaction mixture is no greater than about 150 psig.

15. The process of claim 1, wherein said catalyst is a superacid.

16. The process of claim 15, wherein said catalyst is selected from the group consisting of $SbF_5$, $NbF_5$, and $TaF_5$.

17. The process of claim 16, wherein the concentration of said catalyst in said reaction mixture is no greater than about 5 weight percent of the reaction mixture.

18. The process of claim 16, wherein the mole ratio of the catalyst to HF is about 1:50 to about 1:200.

19. The process of claim 8, herein the concentration of the reaction solvent is about 40 to about 60 wt. % of the reaction mixture.

* * * * *